United States Patent [19]
Greff et al.

[11] Patent Number: 5,620,441
[45] Date of Patent: Apr. 15, 1997

[54] SMOKE EVACUATOR REMOTE ON/OFF SWITCH APPARATUS AND METHOD

[75] Inventors: Richard J. Greff; David W. Tung, both of Yorba Linda, Calif.

[73] Assignee: Stackhouse, Inc., Riverside, Calif.

[21] Appl. No.: 260,084

[22] Filed: Jun. 15, 1994

[51] Int. Cl.$^6$ ........................................... A61B 17/39
[52] U.S. Cl. ............................... 606/32; 606/34; 606/10; 604/35
[58] Field of Search ............................ 606/32–35, 37–42, 606/45–52, 10–12; 604/35, 36

[56] References Cited

U.S. PATENT DOCUMENTS

| | | | |
|---|---|---|---|
| 4,716,897 | 1/1988 | Noguchi et al. | 606/37 |
| 4,788,977 | 12/1988 | Farin et al. | 606/35 |
| 5,108,389 | 4/1992 | Cosmescu . | |
| 5,160,334 | 11/1992 | Billings et al. | 606/38 |
| 5,318,516 | 6/1994 | Cosmescu | 606/38 |

OTHER PUBLICATIONS

"Surgifresh Multi-Stage Air Enhancement System", Surgimedics, 1991 (brochure).

*Primary Examiner*—Angela D. Sykes
*Assistant Examiner*—Michael Peffley
*Attorney, Agent, or Firm*—Richard L. Myers

[57] ABSTRACT

A combination of electrical surgical apparatus includes a first electrical surgical apparatus having a first operative state and a second operative state. A conductor for conducting electrical energy to the first apparatus has first characteristics when the first apparatus is in the first operative state and has second characteristics when the first apparatus is in the second operative state. A sensor is coupled between the first apparatus and a second electrical surgical apparatus having a first operative state and a second operative state. The sensor is responsive to a change from one of the first and second characteristics of the conductor to the other of the first and second characteristics of the conductor to produce a transition signal. A switch coupled between the sensor and the second apparatus is responsive to the transition signal to change the state of the second apparatus from one of the first and second operative states of the second apparatus to the other of the first and second operative states of the second apparatus.

12 Claims, 3 Drawing Sheets

5,620,441

SMOKE EVACUATOR REMOTE ON/OFF SWITCH APPARATUS AND METHOD

BACKGROUND OF THE INVENTION

1. Field of the Invention

This invention relates generally to apparatus for generating smoke in a surgical environment and for evacuating the smoke from the surgical environment, and more specifically to apparatus for automatically controlling the smoke evacuator in response to operation of the smoke generator.

2. Description of the Prior Art

Surgical smoke is often generated in a surgical environment by procedures which include electrosurgical cutting and coagulation, laser ablation, and heating. The smoke which is produced is often unpleasant and strong. It typically comprises water vapor, organic gasses and solid particles. Importantly, it may also contain viruses and virus particles which may represent an infectious potential to the surgical team. As a result, it is considered good surgical practice to remove the smoke from the surgical field to minimize the discomfort and safety risk to the surgical team.

In the past, the systems which produce the smoke and the systems which evacuate the smoke have been maintained separate. Under the circumstances proper evacuation of the smoke has required active participation on the part of a surgical team member to activate the evacuator whenever smoke was has been removed. When this team member failed to activate the evacuator or even delayed activation of the evacuator, the discomfort and safety hazard was quite apparent. When the team member failed to deactivate the evacuator after the smoke had been removed, the useful life of filters and other components of the evacuator was decreased. This lead to increased replacement costs, expensive repairs and down time.

More recently, Billings et al in U.S. Pat. No. 5,160,334, disclosed a combination electrosurgical generator and suction apparatus. This apparatus includes a switching circuit which is actively responsive to either a hand switch or foot switch to power the electrosurgical tool. The switching circuit also controls a motor controller associated with the evacuator.

This system of Billings et al requires that the switching circuit of the electrosurgical apparatus be directly accessed by the motor controller. In other words, one must open the cabinet associated with the electrosurgical generator and determine what signals are present within the switching circuits which can be relied on by the motor controller to control the smoke evacuator. This effort, which typically requires an electronics specialist, is not easily accomplished in the field by technicians which may be faced with many different types of smoke producing systems as well as many types of smoke evacuators. Consequently, the system proposed by Billings et al generally requires the simultaneous manufacture of the electrosurgical apparatus and the smoke evacuator which is then sold as a combined surgical apparatus to the user.

SUMMARY OF THE INVENTION

These problems are overcome by the present invention which relates to an apparatus and method for retrofitting an existing smoke evacuator with apparatus for sensing the operation of a separate electrosurgical system. The system typically includes a generator and a conductor which introduces power from the generator to a hand tool. A passive sensor associated with the present invention includes a transformer core through which the conductor of the electrosurgical system is looped. This coupling of the two systems can be easily accomplished by a medical technician in the field.

When the high frequency current is present in the conductor, the transformer will induce the same high frequency current into a secondary of the transformer. This current is rectified and used to charge a capacitor. When the charge on the capacitor reaches a sufficient level, a transition pulse is generated and an output transistor responsive to the transition pulse closes a switch. A controller associated with the smoke evacuator responses to the momentary closing of the switch to change the state of the evacuator from a deactivated state to an activated state.

The sensor circuit also produces the transition pulse when the charge on the capacitor falls below a predetermined level. Again in response to the transition pulse, the transistor momentarily closes the switch. This discharging of the capacitor occurs when the electrosurgical system is first turned off. The smoke evacuator would have been in the "on" state prior to the event, and will remain in the "on" state through a predetermined period of time required to discharge the capacitor. After this delay, the transition pulse is generated and the switch is closed. Again, the state of the smoke evacuator is changed in response to the closing of this switch. Where the evacuator has been on, now it is turned off after the predetermined period of delay.

This sensor circuit is easily implemented with readily available components and is particularly useful as a retrofit to the smoke evacuator where it can be connected to terminals already available for operation by a foot switch. As noted, the passive sensor circuit can be easily coupled to any electrosurgical system regardless of its type.

These and other features and advantages of the invention will become more apparent with the description of preferred embodiments and the best mode of the invention, and reference to the associated drawings.

DESCRIPTION OF PREFERRED EMBODIMENTS AND THE BEST MODE OF THE INVENTION

Figure 1:
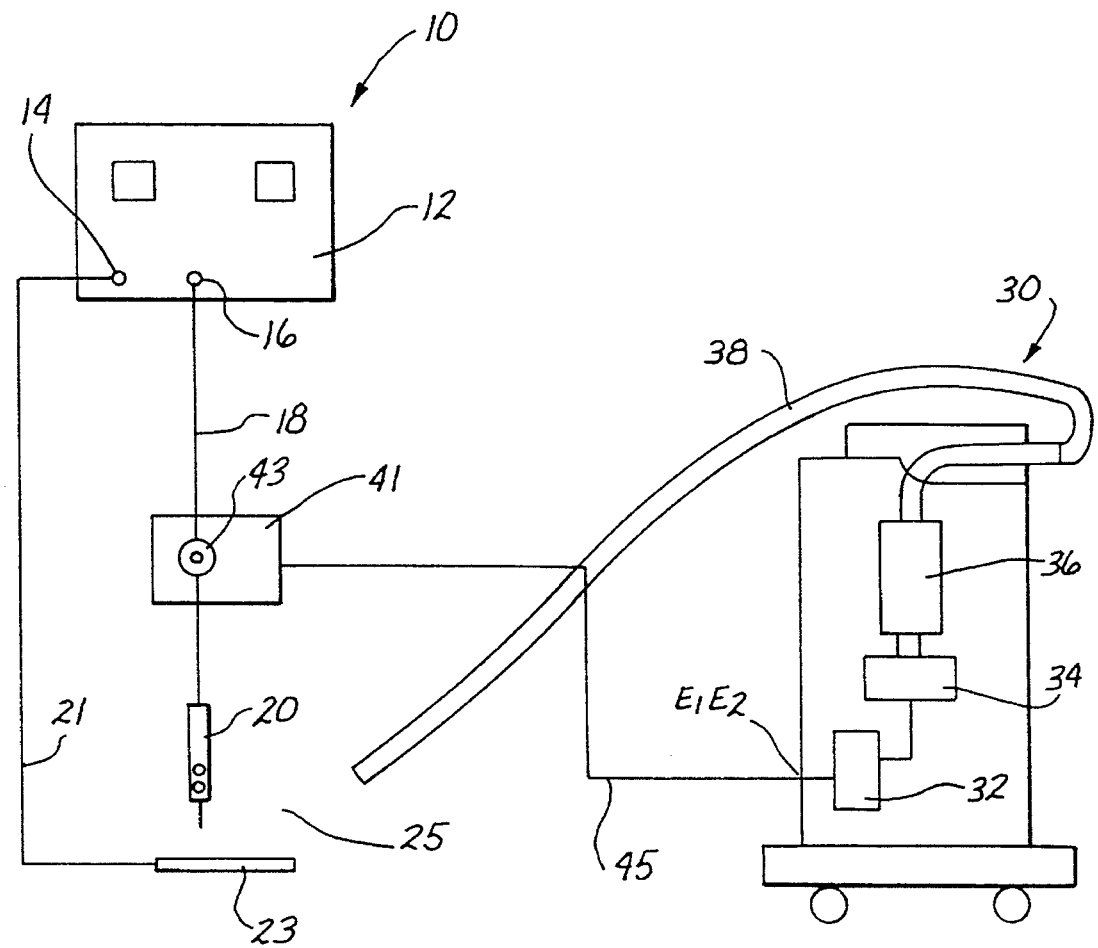
FIG. 1 is a block diagram the sensor of the present invention coupled between a separate electrosurgical system and smoke generator.

An electrosurgical system is illustrated in FIG. 1 and designated by the reference numeral 10. The system 10 includes an electrosurgical generator 12 which provides a high frequency electrosurgical signal across terminal 14 and 16. A conductor 18 couples an electrosurgical handpiece 20 to the terminal 16. A second conductor 21 couples a diffusion pad 23 to the terminal 14. This system is generally referred to as a unipolar system since the handpiece includes only the single conductor 18. It will be apparent to those skilled in the art, however, that the invention is equally applicable to a bi-polar system wherein both of the conductors 18, 21 are present within the handpiece 20. The electrosurgical system 10 can be of the type manufactured by Valleylab and sold under the Model Number SSE2L Force II, or the type manufactured by Aspen and sold under Model Number MF-380.

In operation, a patient (not shown) is laid on the diffusion plate 23, and the handpiece 20 is brought into proximity with tissue at the surgical site. When the generator 12 is activated, the high frequency current flows from the electrode 16 through the conductor 18 and the handpiece 20. This current is concentrated at the point of the handpiece where the highest current density occurs at the surgical site. From this site, the current density defuses greatly as it flows to the wide area of contact presented by the diffusion plate 23. Where the current density is high, at the tip of the handpiece, tissue cells are vaporized resulting in cutting of the tissue. It is this cutting which generates the surgical smoke, illustrated by the lines 25 in FIG. 1, which can be annoying as well as hazardous to the surgical team.

A smoke evacuator 30 is also illustrated in FIG. 1. This evacuator 30 will typically include a motor controller 32, a motor 34 and assorted filters 36, which combine to produce suction through an input tube 38. A vacuum is generated by the motor 34 which draws air including the surgical smoke 25 into the tube 38 where it is deodorized, purified and otherwise cleaned by the filter 36 prior to discharge into the environment. A system typical of this type of smoke evacuator is manufactured by Stackhouse, Inc. under the Model No. ES 2000.

The smoke evacuator 30 can be turned on and off from a control panel or by use of a foot switch (not shown) which is connected to a pair of terminals designated by the letters $E_1$ and $E_2$ in FIG. 1. When continuity exists between the terminals $E_1$, $E_2$, the motor controller 32 changes the state of the smoke evacuator 30. If the evacuator has been on, momentary continuity between the terminals $E_1$ and $E_2$ will result in deactivation of the evacuator 30. If the evacuator 30 has been off, momentary continuity between the terminals $E_1$ and $E_2$ will activate the smoke evacuator 30. Thus, an individual typically steps on the foot switch to turn the evacuator 30 on, and steps on the foot switch again to turn the evacuator 30 off.

Connected between the separate electrosurgical generator 10 and smoke evacuator 30 is a sensing circuit 41 associated with the present invention. The sensing circuit 41 includes a coupler 43 which is attached to the conductor 18. It is of particular advantage that this coupler 43 is not hard wired or actively attached to the conductor 18, but rather is passively coupled to the conductor 18 in the manner described in greater detail below.

The conductor 18 has two states. In a first state, the electrosurgical power is present on the conductor 18 between the generator 12 and the handpiece 20. In a second state, power is absent from the conductor 18 between the generator 12 and the handpiece 20. It is the purpose of the circuit 41 to sense a change in the state of the conductor 18. Where power has been present on the conductor 18, the circuit 41 senses the absence of that power. Where there has been no power present on the conductor 18, the circuit 41 senses the presence of power on the conductor 18. In either case, a signal is output through a conductor cable 45 which is plugged into the terminals $E_1$ and $E_2$ of the smoke evacuator 30. It will be apparent to those skilled in the art that this sensing circuit 41 is equally advantageous when the sensor 43 is coupled to the conductor 21 which carries a return current from the plate 23. This conductor 21 also has the two states previously discussed.

Figure 2:
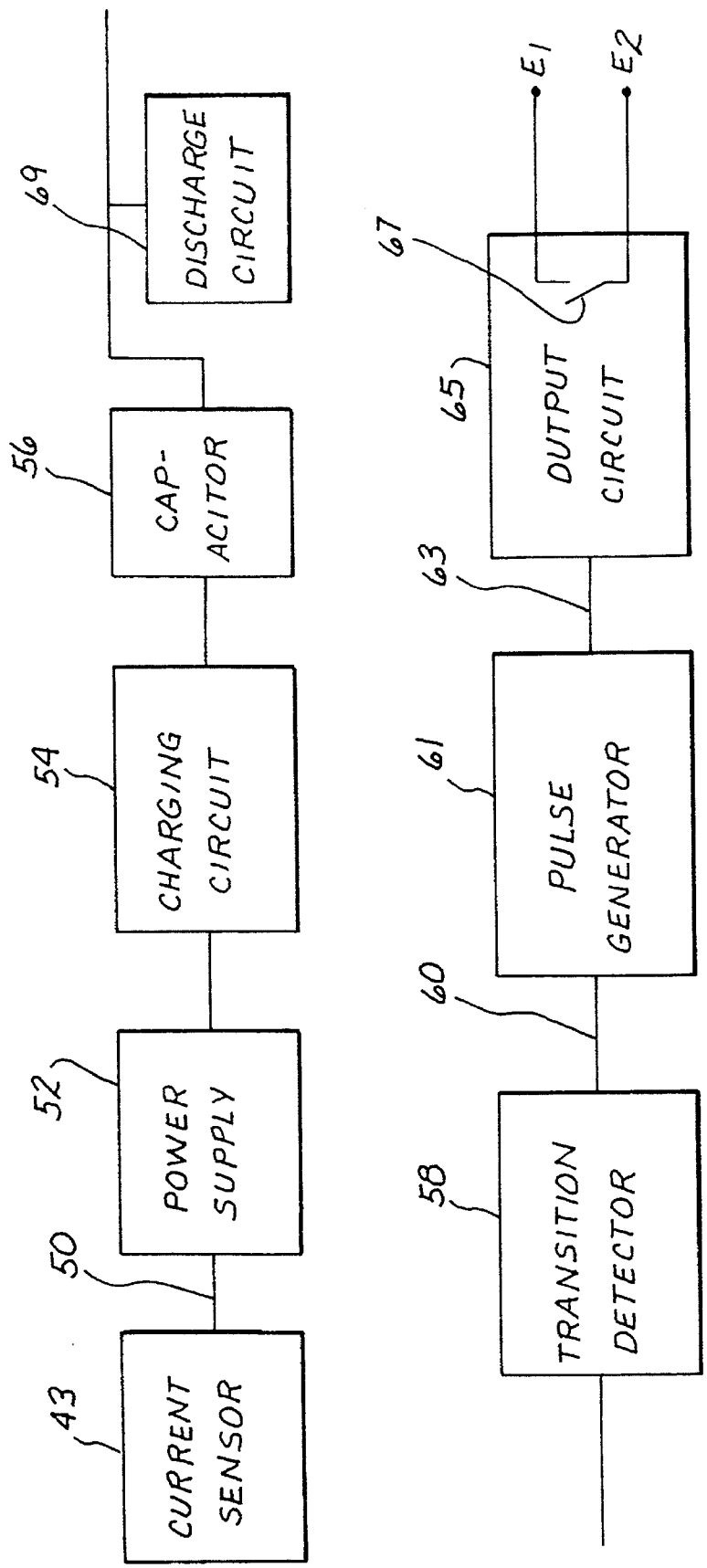
FIG. 2 is a block diagram of the sensor circuit illustrated in FIG. 1.

A block diagram associated with the sensor circuit 41 is illustrated in FIG. 2. This embodiment of the sensing circuit 41 includes the current sensor 43, which provides an output on a conductor 50 to a power supply 52. When current is sensed by the sensor 43, the power supply 52 activates a charging circuit 54 which charges a capacitor 56. When the charge on the capacitor 56 rises to a predetermined level, a transition detector 58 outputs a transition signal on a conductor 60 to a pulse generator 61. The pulse from the generator 61 is similarly output on a conductor 63 to an output circuit 65 which includes a switch 67. This switch 67 is connected through the cable 45 across the terminals $E_1$, $E_2$ of the smoke evacuator 30.

When current is no longer sensed on the conductor 18 by the sensor 43, charging of the capacitor 56 ceases. If the charge is not maintained, the capacitor 56 is free to discharge through a discharge circuit 69 until it falls below a predetermined magnitude. This event is also detected by the transition detector 58 and the transition signal is output on the conductor 60. The pulse generator 61 outputs a pulse on the conductor 63 and the output circuit 65 momentarily closes the switch 67. This closing of the switch 67 occurs after a predetermined delay which is related to the characteristics of the discharge circuit 69. When the switch 67 is closed, continuity exists between the terminals $E_1$ and $E_2$, and the motor controller 32 deactivates the evacuator 30.

Figure 3:
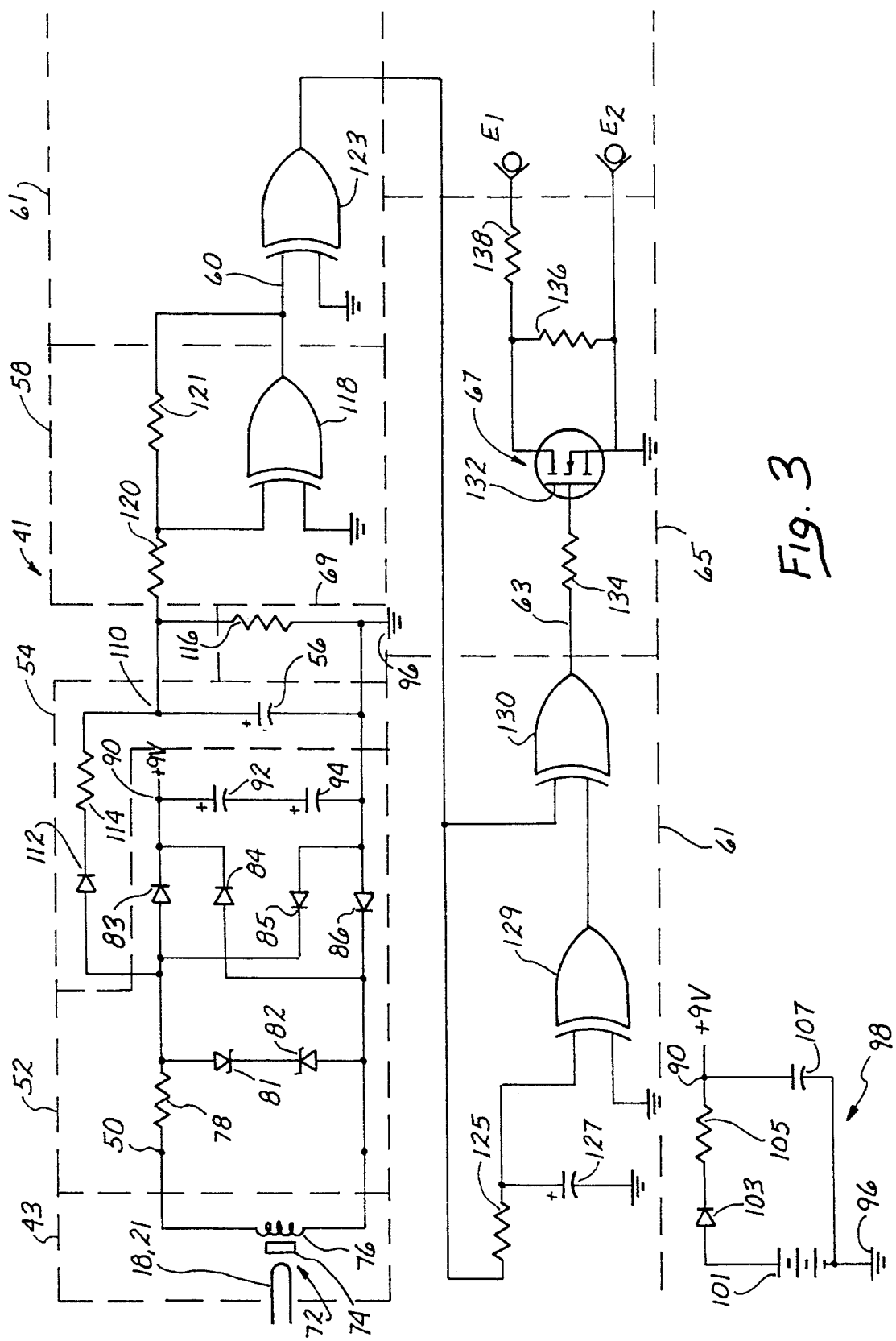
FIG. 3 is a schematic diagram view of a preferred embodiment of the sensor circuit illustrated in FIG. 2.

A preferred embodiment of the sensor circuit 41 is illustrated in greater detail in the schematic of FIG. 3. In this embodiment, the current sensor 43 includes a transformer 72 having a transformer core 74 and a secondary winding 76. The conductor to be monitored, either the conductor 18 or 21, is looped passively through the core 74 of the transformer 72. When the high frequency power output by the electrosurgical generator 12 is introduced onto the conductor 18, the high frequency current, typically 0.5 to 3.0 megahertz, it passed through the conductors 18, 21. This current is passively induced through the core 74 to the secondary winding 76 of the transformer 72. It is this current on the conductor 50 which is introduced to the power supply 52 through a current limiting resistor 78.

The power supply 52 includes six diodes designated by the reference numerals 81–86. Diodes 81 and 82 can be chosen with characteristics suitable to limit the high frequency current in the secondary circuit to about 9 volts AC. Diodes 83–86 form a full wave bridge rectifier which provides an output on terminal 90. A pair of capacitors 92, 94 are connected in series between the terminal 90 and ground 96.

Since the entire sensing circuit 41 only consumes about one microamp of current, the charge on capacitors 92 and 94 can be stored for a significant length of time, such as one month. The charge on these capacitors 92, 94 is replenished whenever high frequency current is sensed on the conductor 18 or 21.

If the capacitors 92, 94 are allowed to discharge, a small time delay will normally be encountered when the circuit is first activated and the charge reestablished. If such a delay is objectionable, an optional battery circuit 98 may be of advantage if the unit is likely to sit idle for long periods of time. This circuit 98 includes a battery 101 which is connected through a blocking diode 103 and a resistor 105 to the terminal 90. A capacitor 107 is connected between the terminal 90 and ground 96. In this battery circuit 98, the diode 103 functions to prevent circuit damage in the event of a reversed battery condition.

In an embodiment wherein the capacitor 56 is connected between a terminal 110 and ground 96, the 9 volts DC provided by either the full wave bridge rectifier or the battery circuit 98 is present across the terminals 90 and 110.

The charging circuit 54 includes a diode 112 which is serially connected through a resistor 114 to the terminal 110. The current from the secondary winding 76 of the transformer 72 is rectified by the diode 112 and used to charge the capacitor 56 through the resistor 114. The capacitor 56 is connected in parallel with a resistor 116 which forms the discharge circuit 69 discussed in greater detail below.

The charge on the capacitor 56 is introduced to the transition detector 58 which includes a NOR GATE 118 and biasing resistors 120 and 121. The output of the NOR GATE 118 is introduced to a second NOR GATE 123 which similarly introduces its output to a resistor 125 and across a capacitor 127 into a third NOR GATE 129. The output of the third NOR GATE 129 is presented to a fourth NOR GATE 130.

When the high frequency is sensed by the transition detector 58, the NOR GATE 118 transitions from a low state to a high state. This results in the NOR GATES 123, 129 and 130 producing a pulse on the conductor 63. The duration of this pulse is determined by the values of the resistor 125 and the capacitor 127.

When the high frequency current is removed from the conductor 18 or 21, the capacitor 56 discharges through the resistor 116. The value of this resistor 116 determines the delay time associated with the discharge. When the magnitude of the charge on the capacitor 56 falls below a predetermined level, associated with the desired delay, the NOR GATE 118 transitions back from the high state to the low state. The pulse generator responds to the transition signal on conductor 60 in the same manner as that previously discussed. Thus the NOR GATES 123, 129 and 130 produce a pulse on the conductor 63 as the NOR GATE 118 transitions from the high state to the low state. Accordingly, a pulse is generated on the conductor 63 with each transition of the output of NOR GATE 118. A transition signal occurs on the conductor 60 whether the NOR GATE 118 is transitioning from a low state to a high state or from a high state to a low state.

The output circuit 65 includes the switch 67 in the form of a transistor 132 together with a biasing resistor 134. This output transistor 132 provides a circuit closure on terminals $E_1$ and $E_2$ whenever a pulse is generated by the NOR GATE 130. Resistors 136 and 138 are provided at the output of the transistor 132 for current limiting and static protection. The circuit closure provided by the transistor 132 is sensed as continuity between the terminals $E_1$ and $E_2$ by the motor controller 32 of the smoke evacuator 30.

The sensing circuit 41 of the present invention is of particular value in retrofitting an existing smoke evacuator for automatic operation in response to an existing electrosurgical generator 12. Since it is passively coupled to the generator 12, the sensing circuit 41 does not require connection by a person having superior electronic skills. This connection can easily be accomplished by any member of the surgical team who merely loops the conductor 18 through the core 74 of the transformer. The conductor 45 from the sensing circuit 41 is merely plugged into an existing connector on the evacuator 30 where the terminals $E_1$ and $E_2$ are presented for alternative operation with a foot switch (not shown). The circuit has a very low current drain making it particularly applicable for use as infrequently as once a month. Alternatively, the battery circuit 98 can be provided if an additional recharge time is objectionable. The circuit is simplified by the fact that the pulse generator 61 and output circuit 65 function the same whether the smoke evacuator 30 is to be activated or deactivated. Thus, a simple charge circuit can be relied on to transition the detector 58 to a high state and a simple discharge circuit 69 can be relied on to transition the detector 58 to the low state.

From the foregoing discussion it will be apparent that the sensor circuit 41 can be embodied in forms other than those disclosed. For example, a bipolar electrosurgical system can also be sensed by the circuit 41 to automatically activate and deactivate the evacuator 30. Sensors other than the transformer 72 could also be provided to passively indicate whether high frequency current is present or absent from the conductor 18. Circuits other than that disclosed for the transition detector 58 will also be apparent for responding to a change in the state of any signal present on the conductor 18. Other circuits will also be apparent for generating a pulse or other signal in response to transition detection.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. Apparatus for controlling operation of a smoke evacuator in response to operation of a surgical tool, which produces smoke as a side effect when performing a surgical function, comprising:

an electrosurgical power generator for activating the surgical tool in order to perform a surgical function at a surgical site;

means coupled to the power generator for introducing the power from the generator to the tool to enable the tool to perform a surgical function at the surgical site, the introducing means having a first state when the power is being introduced to the tool and a second state when the power is not being introduced to the tool;

sensor means coupled to the introducing means and responsive to the introduction of power from the generator to the tool for producing a transition signal when the introducing means changes state from one of the first state and the second state to the other of the first state and second state;

switch means including a switch and being responsive to the transition signal for momentarily closing the switch when the introducing means changes state;

a smoke evacuator for removing from the surgical site smoke produced by the surgical tool, the evacuator having an activated state and a deactivated state; and control means included in the evacuator and responsive to momentary closure of the switch by the switch means for changing the state of the evacuator from one of the activated state and deactivated state to the other of the activated state and deactivated state.

2. The apparatus recited in claim 1 wherein the sensor means comprises:

a capacitor;

means for charging the capacitor when the introducing means is in the first state; and means responsive to the capacitor for producing the transition signal when the charge on the capacitor is not less than a first magnitude.

3. The apparatus recited in claim 2 wherein the sensor means further comprises:

means for discharging the capacitor when the introducing means is in the second state; and the producing means includes means responsive to the capacitor for producing the transition signal when the charge on the capacitor is not greater than a second magnitude.

4. The apparatus recited in claim 3 wherein the discharging means includes:

means for delaying the discharge of the capacitor so that the charge on the capacitor decays from the first magnitude to the second magnitude over a predetermined period of time.

5. The apparatus recited in claim 1 wherein:

the introducing means includes a conductor for introducing the power from the generator to the tool to enable the tool to perform the surgical function at the surgical site; and the sensing means includes a passive sensor responsive to each of the presence and absence of the power in the conductor to produce the transition signal.

6. A method for controlling operation of a surgical tool, which produces smoke as a side effect when performing a surgical function, and a surgical evacuator for removing the smoke, comprising the steps of:

generating power for the surgical tool;

introducing the power to the surgical tool through a conductor to enable the tool to perform a surgical function at a surgical site;

ceasing power introduction to the tool to inhibit the tool from performing the surgical function at the surgical site;

passively sensing the conductor to detect one of the introduction of power to the tool and the ceasing of power introduction to the tool to thereby generate a transition signal; and controlling the smoke evacuator in response to the transition signal to change the smoke evacuator from one of an activated state and a deactivated state to the other of the activated state and the deactivated state.

7. The method recited in claim 6 wherein the sensing step comprises the steps of:

providing a capacitor;

charging the capacitor during the introducing step;

sensing the charge on the capacitor; and generating the transition signal when the charge on the capacitor is not less than a first level.

8. The method recited in claim 7 wherein the sensing step further comprises the steps of:

discharging the capacitor during the ceasing step; and generating the transition signal when the charge sensed on the capacitor is greater than a second level.

9. The method recited in claim 8 wherein the sensing step further comprises the step of:

delaying the discharge of the capacitor from the first magnitude to the second magnitude for a predetermined period of time.

10. The method recited in claim 6 wherein the sensing step includes the step of passively sensing one of the introducing step and the ceasing step to generate the transition signal.

11. An apparatus for retrofitting a conventional manually-controlled smoke evacuator to thereby achieve an automatically-controlled smoke evacuator, the automatically-controlled smoke evacuator activating or deactivating a smoke evacuator according to a state of an electrosurgical generator, the apparatus comprising:

(a) a sensing circuit for passively coupling to a conventional conductor, the conductor connecting a conventional high-frequency electrosurgical generator to one of a diffusion pad and a conventional hand piece, the sensing circuit detecting a current of the conventional conductor and comprising:

(1) a transformer core;

(2) a secondary winding in electrical communication with the core;

(3) an aperture in the transformer core for accommodating a portion of the conventional conductor and a high-frequency current on the conventional conductor, wherein the high-frequency current on the conventional conductor is passively induced through the transformer core to the secondary winding;

(4) a rectifying diode in electrical communication with the secondary winding for rectifying the passively-induced current from the secondary winding;

(5) a capacitor connected to the rectifying diode, for receiving the rectified, passively-induced current from rectifying diode, and for developing a charge from the received, rectified, passively-induced current from rectifying diode;

(6) a resistor connected to the capacitor for discharging any charge accumulated on the capacitor from the received, rectified, passively-induced current, wherein the capacitor develops a net positive charge when the received, rectified, passively-induced current is applied to the capacitor and develops a net zero charge when the received, rectified, passively-induced current from rectifying diode is not applied to the capacitor;

(7) a transition detector in electrical communication with the capacitor for outputting a transition signal each time that a charge on the capacitor rises above a first predetermined threshold level, and for outputting a transition signal each time that the charge on the capacitor falls below a second predetermined threshold level;

(8) a pulse generator in electrical communication with the transition detector for generating and outputting a predetermined pulse each time the transition detector outputs a transition signal; and (9) a switch for providing a momentary circuit closure between two output terminals, $E_1$ and $E_2$, each time that the pulse generator generates and outputs the predetermined pulse; and (b) a conductor cable housing the two output terminals, $E_1$ and $E_2$, and connecting the sensing circuit to a conventional smoke evacuator, the conventional smoke evacuator being switchable between an on-mode and an off-mode each time that the momentary circuit closure between the two terminals $E_1$ and $E_2$ is provided by the switch.

12. The apparatus for automatically activating or deactivating a smoke evacuator, according to claim 11, wherein the transition detector comprises a NOR gate, the NOR gate having a first input terminal grounded and a second input terminal attached to the capacitor, wherein when the charge on the capacitor rises above the first predetermined threshold level the NOR gate compares a logical "0" with a logical "0" and outputs a logical "1," and wherein when the charge on the capacitor falls below the second predetermined threshold level the NOR gate compares a logical "0" with a logical "1" and outputs a logical "0," and wherein the pulse generator generates and outputs the predetermined pulse each time the transition detector outputs one of the logical "0" and the logical "1."

* * * * *